(12) United States Patent
Qiu et al.

(10) Patent No.: US 12,110,323 B2
(45) Date of Patent: Oct. 8, 2024

(54) ANTI-HUMAN INTERLEUKIN 17A MONOCLONAL ANTIBODY AND APPLICATION THEREOF

(71) Applicant: JIANGSU QYUNS THERAPEUTICS CO., LTD., Jiangsu (CN)

(72) Inventors: Jiwan Qiu, Jiangsu (CN); Zhihua Qiu, Jiangsu (CN); Wei Chen, Jiangsu (CN); Tao Chen, Jiangsu (CN); Yong Kong, Jiangsu (CN); Yiliang Wu, Jiangsu (CN)

(73) Assignee: JIANGSU QYUNS THERAPEUTICS CO., LTD., Jiangsu (CN)

( * ) Notice: Subject to any disclaimer, the term of this patent is extended or adjusted under 35 U.S.C. 154(b) by 997 days.

(21) Appl. No.: 17/055,789

(22) PCT Filed: May 17, 2018

(86) PCT No.: PCT/CN2018/087271
§ 371 (c)(1),
(2) Date: Nov. 16, 2020

(87) PCT Pub. No.: WO2019/218298
PCT Pub. Date: Nov. 21, 2019

(65) Prior Publication Data
US 2021/0230264 A1 Jul. 29, 2021

(51) Int. Cl.
*C07K 16/24* (2006.01)
*A61K 39/00* (2006.01)
*A61P 37/06* (2006.01)

(52) U.S. Cl.
CPC ............ *C07K 16/244* (2013.01); *A61P 37/06* (2018.01); *A61K 2039/505* (2013.01); *C07K 2317/34* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| CN | 101326195 | 12/2008 |
|---|---|---|
| CN | 101611057 | 12/2009 |
| CN | 102164959 | 8/2011 |
| CN | 105073775 | 11/2015 |
| CN | 106336459 | 1/2017 |
| CN | 107488227 | 12/2017 |
| EP | 2 864 355 | 10/2016 |
| EP | 3 470 427 | 4/2019 |
| WO | 2007/070750 | 6/2007 |
| WO | 2007/149032 | 12/2007 |
| WO | 2010/034443 | 4/2010 |
| WO | 2011/053763 | 5/2011 |
| WO | 2014/122613 | 8/2014 |
| WO | 2015/198217 | 12/2015 |
| WO | 2017/011260 | 1/2017 |

OTHER PUBLICATIONS

Prabhala, R. H., et al., "Targeting IL-17A in Multiple Myeloma: A Potential Novel Therapeutic Approach in Myeloma", Leukemia, 2016, vol. 30, No. 2, pp. 379-389.
McInnes, I. B., et al., "Secukinumab, a human anti-interleukin-17A monoclonal antibody, in patients with psoriatic arthritis (Future 2): a randomised, double-blind, placebo-controlled, phase 3 trial", The Lancet, 2015, vol. 386, No. 9999, pp. 1137-1146.
Tsuda, K., et al., "Ixekizumab for psoriasis", The Lancet, 2016, vol. 387, No. 10015,pp. 225-226.
Anette, K., et al., " Secukinumab, a novel anti-IL-17A antibody, shows low immunogenicity potential in human in vitro assays comparable to other marketed biotherpeutics with low clinical immunogenicity", MABS, 2016, vol. 8, No. 3, pp. 536-550.
International Search Report issued Feb. 14, 2019 in International (PCT) Application No. PCT/CN2018/087271.
Xu et al., "Preparation and Activity Detection of A Novel Monoclonal Antibody to Human Interleukin-17RA", Acta Academiae Medicinae Sinicae, 2016, vol. 38, No. 4, pp. 428-433, with English Abstract.
Wang Xu, et al., "Inhibition and Its Mechanism of Anti-il-17a Monoclonal Antibody against Fibrotic Lesion of Mice with Systemic Sclerosing Disease", 2015, Shandong Medical Journal, vol. 56, No. 48, pp. 38-41, with English Abstract.

*Primary Examiner* — Ruixiang Li
(74) *Attorney, Agent, or Firm* — Wenderoth, Lind & Ponack, L.L.P.

(57) ABSTRACT

Disclosed by the present invention are an anti-human interleukin 17A monoclonal antibody and an application thereof. The epitope of the monoclonal antibody binding to human interleukin 17A comprises 78th asparagine (N78). The antibody may be used to treat rheumatoid arthritis, psoriasis, multiple sclerosis, psoriatic arthritis, plaque psoriasis and/or ankylosing spondylitis.

12 Claims, 5 Drawing Sheets
Specification includes a Sequence Listing.

```
                         10        20        30        40        50        60        70
                         |         |         |         |         |         |         |
         human     GITIPRNPGCPNSEDKNFPKTVMVNLNIHNRNTNTNPKRSSDYYNRSTSPWNLHRNEDPERYPSVIWEAK
 rhesus monkey     GIAIPRNPGCPNSEDKTFPKTVMVNLNIHNRNTNINPKRSSDYYNRSTSPWNLHRNEDPERYPSVIWEAK
cynomolgus monkey  GIAIPRNSGCPNSEDKNFPKTVMVNLNIHNRNTSINPKRSSDYYNRSTSPWNLHRNEDPERYPSVIWEAK
                     *    *       *              *

80        90       100       110       120       130
                         |         |         |         |         |         |
         human     CRHLGCINADGNVDYHMNSVPIQQEILVLRREPPHCPNSFRLEKILVSVGCTCVTPIVHHVA
 rhesus monkey     CRHLGCVNADGNVDYHMNSVPIQQEILVLRREPPHCPNSFRLEKILVSVGCTCVTPIVHHVA
cynomolgus monkey  CRHLGCVKADGNVDYHMNSVPIQQEILVLRREPPHCPNSFRLEKILVSVGCTCVTPIVHHVA
                        **                    *
```

ANTI-HUMAN INTERLEUKIN 17A MONOCLONAL ANTIBODY AND APPLICATION THEREOF

FIELD OF THE INVENTION

The present invention relates to the field of antibody drugs. Specifically, the present invention relates to a monoclonal antibody against human interleukin 17A and a use thereof.

BACKGROUND OF THE INVENTION

Interleukin 17 (IL-17), also known as CTLA-8 or IL-17A, is a pro-inflammatory cytokine that stimulates non-immune cells such as fibroblasts, keratinocytes, epithelial and endothelial cells, synovial cells, etc. to secrete IL-6, IL-8, PGE2, MCP-1, CXCL-1 and G-CSF and other cytokines, and also has the biological effects of inducing the surface expression of ICAM-1 and T cell proliferation, etc. IL-17A is mainly produced by a type of activated $CD^{4+}$ T cells called Th17 and acts by binding to the complex of IL-17RA and IL-17RC (Toy et al., 2006, J. Immunol. 177(11); 36-39).

So far, six members of IL-17 family have been discovered: IL-17A (IL-17), IL-171, IL-17C, IL-17D, IL-17E (IL-25), and IL-17F. These interleukin-17 cytokines can bind to the corresponding receptors to mediate different inflammatory responses.

Among them, IL-17A is a homodimer composed of two chains of 155 amino acids connected by disulfide bonds, with a molecular weight of 35 kDa. The structure of IL-17 is composed of a signal peptide (AA) consisting of 23 amino acids and a chain region of 132 amino acids.

Overexpression of IL-17A can cause many inflammatory diseases. For example, IL-17A acts on macrophages and DC cells to induce high expression of IL-1, IL-6, TNF and CRP, leading to inflammation, and participates in the pathological process of psoriasis and transplant rejection; IL-17A acts on endothelial cells to induce high expression of IL-6, MMP and coagulation factors, leading to vascular activation, and participates in the pathological process of reperfusion injury, thrombus and atherosclerosis; IL-17A acts on fibroblasts to induce high expression of IL-6, chemokines, growth factors and MMP, leading to matrix destruction, and participates in the pathological process of multiple sclerosis and Crohn's disease: IL-17A acts on osteoblasts and chondrocytes to induce RANKL, MMP, osteoclast production, leading to bone erosion, cartilage damage, and participates in the pathological process of rheumatic arthritis and periodontal disease (N Engl J Med. 2009 Aug. 27; 361(9):888-98. Nat Rev Drug Discov. 2012Oct: 11(10):763-76. Semin Arthritis Rheum. 2013Oct; 43(2):158-70. Trends Mol Med. 2016Mar: 22(3):230-41.).

IL-17A neutralizing antibodies can inhibit the high expression of IL-17A in patients with autoimmune diseases and reduce the production of IL-6, an important inflammatory factor (ChabaudM, DurandJM. BuchsN, et al. Arthritis Rheum. 1999, 42:963-70). Many animal model experiments of autoimmune diseases have proved that the use of antibodies to neutralize IL-17A can effectively inhibit the pathological development of inflammation (LubbertsE, KoendersMl, Oppers-Walgreen B, et al. Arthritis Rheum., 2004, 50:650-659).

At present, IL-17A-related antibody drugs have been approved for marketing. They are Secukinumab (IL-17A targeting antibody, SEC) for the treatment of plaque psoriasis, ankylosing spondylitis and psoriatic arthritis, and Ixekizumab (IL-17A targeting antibody, IXE), used to treat plaque psoriasis and psoriatic arthritis.

SUMMARY OF THE INVENTION

The purpose of the present invention is to provide a new anti-human interleukin 17A monoclonal antibody, a pharmaceutical composition containing the monoclonal antibody, and the pharmaceutical use of the monoclonal antibody.

That is, the present invention includes:

1. An isolated anti-human interleukin 17A monoclonal antibody, which binds to an epitope including asparagine (N78) at position 78th in human interleukin 17A. As far as the inventor knows, none of the human interleukin 17A epitopes bound by anti-human interleukin 17A monoclonal antibody in the prior art contains the 78th asparagine (N78).

2. The monoclonal antibody of any one of the aforementioned items, which binds to an epitope including $G_{75}XXN_{78}XD_{80}XN_{82}V_{83}D_{84}Y_{85}$ in human interleukin 17A, wherein X represents any amino acid.

3. The monoclonal antibody of any one of the aforementioned items, which binds to an epitope including $G_{75}G_{76}XN_{78}XD_{80}XN_{82}V_{83}D_{84}Y_{85}$ in human interleukin 17A, wherein X represents any amino acid.

4. The monoclonal antibody of any one of the aforementioned items, which binds to an epitope including $G_{75}C_{76}I_{77}N_{78}A_{79}D_{80}G_{81}N_{82}V_{83}D_{84}Y_{85}$ in human interleukin 17A.

5. The monoclonal antibody of any one of the aforementioned items, comprising three heavy chain complementarity determining regions (CDR-H1, CDR-H2 and CDR-H3) and three light chain complementarity determining regions (CDR-L1, CDR-L2 and CDR-L3), wherein, (a) an amino acid sequence of the CDR-H1 is the amino acid sequence shown in SEQ ID NO:1, or an amino acid sequence obtained by deleting, substituting, and/or adding one or more amino acids in the amino acid sequence shown in SEQ ID NO:1, or an amino acid sequence having more than 50% identity with the amino acid sequence shown in SEQ ID NO: 1;

(b) an amino acid sequence of CDR-H2 is the amino acid sequence shown in SEQ ID NO: 2, or an amino acid sequence obtained by deleting, substituting, and/or adding one or more amino acids in the amino acid sequence shown in SEQ ID NO: 2, or an amino acid sequence having more than 50% identity with the amino acid sequence shown in SEQ ID NO: 2;

(c) an amino acid sequence of CDR-H3 is the amino acid sequence shown in SEQ ID NO: 3, or an amino acid sequence obtained by deleting, substituting, and/or adding one or more amino acids in the amino acid sequence shown in SEQ ID NO: 3, or an amino acid sequence having more than 50% identity with the amino acid sequence shown in SEQ ID NO: 3;

(d) an amino acid sequence of CDR-L1 is the amino acid sequence shown in SEQ ID NO: 4, or an amino acid sequence obtained by deleting, substituting, and/or adding one or more amino acids in the amino acid sequence shown in SEQ ID NO: 4, or an amino acid sequence having more than 50% identity with the amino acid sequence shown in SEQ ID NO: 4;

(e) an amino acid sequence of CDR-L2 is the amino acid sequence shown in SEQ ID NO: 5, or an amino acid sequence obtained by deleting, substituting, and/or adding one or more amino acids in the amino acid sequence shown in SEQ ID NO: 5, or an amino acid sequence having more than 50% identity with the amino acid sequence shown in SEQ ID NO: 5; and (f) an amino acid sequence of CDR-L3 is the amino acid sequence shown in SEQ ID NO: 6, or an amino acid sequence obtained by deleting, substituting, and/or adding one or more amino acids in the amino acid sequence shown in SEQ ID NO: 6, or an amino acid sequence having more than 50% identity with the amino acid sequence shown in SEQ ID NO:6.

Here, the "more amino acids" refers to, for example, 30, 20, 15, 10, 5, 3, or 2 amino acids.

The "more than 50% identity" refers to, for example, more than 70%, more than 80%, more than 90%, more than 95%, more than 96%, more than 97%, more than 98%, or more than 99% identity. In this specification. "identity" means: for example, in FASTA3 [Science, 227, 1435-1441 (1985); Proc. Natl. Acad. Sci. USA, 85, 2444-2448 (1988)], which is a homology search program known to those skilled in the art, the values calculated by using the default (initial setting) parameters.

The "substitution" is preferably a "conservative substitution", that is, the amino acid residue to be mutated is mutated to other amino acids that retain the properties of the amino acid side chain (this process is known as conservative amino acid substitution). Examples of amino acid side chain properties include hydrophobic amino acids (A, I, L, M, F, P, W, Y, V), hydrophilic amino acids (R, D, N, C, E, Q, G, H, K, S, T) and side chains with the following common functional groups or characteristics: aliphatic side chains (G, A, V, L, I, P); hydroxyl-containing side chains (S, T, Y); side chains containing sulfur atoms (C, M); side chains containing carboxylic acid and amide (D, N, E, Q); side chains containing base (R, K, H) and side chains containing aromatic (F, Y, W). It should be noted that the letters in parentheses represent single-letter symbols for amino acids.

Conservative substitutions that give functionally similar amino acids are well known in the art. For example, the amino acids in the following 8 groups constitute conservatively substituted amino acids for each other:

1) Alanine (A), Glycine (G);
2) Aspartic acid (D), glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

6. The monoclonal antibody of any one of the aforementioned items, wherein:

(a) the amino acid sequence of CDR-H1 is the amino acid sequence shown in SEQ ID NO:1;
(b) the amino acid sequence of CDR-H2 is the amino acid sequence shown in SEQ ID NO: 2;
(c) the amino acid sequence of CDR-H3 is the amino acid sequence shown in SEQ ID NO: 3;
(d) the amino acid sequence of CDR-L1 is the amino acid sequence shown in SEQ ID NO: 4;
(e) the amino acid sequence of CDR-L2 is the amino acid sequence shown in SEQ ID NO: 5; and
(f) the amino acid sequence of CDR-L3 is the amino acid sequence shown in SEQ ID NO:6.

7. An isolated anti-human interleukin 17A monoclonal antibody, which comprises three heavy chain complementarity determining regions (CDR-H1, CDR-H2 and CDR-H3) and three light chain complementarity determining regions (CDR-L1, CDR-L2 and CDR-L3), wherein, (a) an amino acid sequence of CDR-H1 is the amino acid sequence shown in SEQ ID NO: 1;
(b) an amino acid sequence of CDR-H2 is the amino acid sequence shown in SEQ ID NO: 2;
(c) an amino acid sequence of CDR-H3 is the amino acid sequence shown in SEQ ID NO: 3;
(d) an amino acid sequence of CDR-L1 is the amino acid sequence shown in SEQ ID NO: 4;
(e) an amino acid sequence of CDR-L2 is the amino acid sequence shown in SEQ ID NO: 5; and
(f) an amino acid sequence of CDR-L3 is the amino acid sequence shown in SEQ ID NO:6.

8. An isolated anti-human interleukin 17A monoclonal antibody, which competes with the monoclonal antibody of item 7 for binding to human interleukin 17A.

9. An isolated anti-human interleukin 17A monoclonal antibody, which binds to the same epitope in human interleukin 17A as the monoclonal antibody of item 7.

10. An isolated nucleic acid, encoding the monoclonal antibody of any one of the aforementioned items.

11. A host cell, comprising the nucleic acid of item 10.

The nucleic acid may be present on a vector. The vector may be of any type, for example, a recombinant vector such as an expression vector. Any one of a variety of host cells can be used. In one embodiment, the host cell is a prokaryotic cell, for example, E. coli. In another embodiment, the host cell is a eukaryotic cell, for example, a mammalian cell, such as a Chinese Hamster Ovary (CHO) cell.

12. A method of producing a monoclonal antibody, comprising culturing the host cell of item 11 to produce the monoclonal antibody of any one of the aforementioned items.

13. A pharmaceutical composition, comprising the monoclonal antibody of any one of the aforementioned items and a pharmaceutically acceptable carrier. The pharmaceutical composition may further comprise additional therapeutic agents (for example, different anti-human interleukin 17A antibodies).

14. The pharmaceutical composition according to item 13, which is used for autoimmune diseases, such as treatment of rheumatoid arthritis, psoriasis. Crohn's disease, multiple sclerosis, psoriatic arthritis, plaque psoriasis and/or ankylosing spondylitis.

15. Use of the monoclonal antibody of any one of the aforementioned items in the preparation of a medicament for the treatment of autoimmune diseases, such as the treatment of rheumatoid arthritis, psoriasis, Crohn's disease, multiple sclerosis, psoriatic arthritis, plaque psoriasis and/or ankylosing spondylitis.

16. A method of treating an autoimmune disease, which includes:

the monoclonal antibody according to any one of claims 1 to 9 or the pharmaceutical composition according to claim 13 is administered to a subject in need thereof.

17. The method according to claim 16, wherein the autoimmune disease is rheumatoid arthritis, psoriasis, Crohn's disease, multiple sclerosis, psoriatic arthritis, plaque psoriasis and/or ankylosing spondylitis.

EFFECT OF THE INVENTION

The present invention provides a new anti-human interleukin 17A monoclonal antibody, compared with the existing anti-human interleukin 17A monoclonal antibody, its binding affinity to IL-17A is equivalent or higher.

DETAIL DESCRIPTION OF THE INVENTION

Definitions

The scientific and technological terms mentioned in this specification have the same meaning as those commonly understood by those skilled in the art. In case of conflict, the definition in this specification shall prevail.

Generally, the terms used in this specification have the following meanings.

In this specification, an "isolated" antibody is an antibody that has been separated from a component of its natural environment. In certain embodiments, the antibody is purified to greater than 95% or 99% purity which is determined by, for example, electrophoresis (for example, SDS-PAGE isoelectric focusing (IEF), capillary electrophoresis) or chromatography (for example, ion exchange or reverse phase HPLC). For a review of methods for evaluating antibody purity, see, for example, Flatman et al., J. Chromatogr. B848:79-87 (2007).

In the present specification, "monoclonal antibody" means an antibody derived from a population of substantially homologous antibodies, that is, each antibody constituting the population is the same and/or binds the same epitope, except for possible variant antibodies (For example, containing naturally occurring mutations or produced during the production of monoclonal antibody products), such variants are usually present in trace amounts. Unlike polyclonal antibody preparations which usually include different antibodies directed against different determinants (epitopes), each monoclonal antibody of the monoclonal antibody preparation is directed against a single determinant on the antigen. Thus, the modifier "monoclonal" indicates the characteristic that the antibody is derived from a substantially homologous antibody population, and should not be interpreted as requiring the production of the antibody by any specific method. For example, the monoclonal antibody to be used in accordance with the present invention can be prepared by a variety of techniques including, but not limited to, hybridoma methods, recombinant DNA methods, phage display methods, and methods of using a transgenic animal containing all or part of a human immunoglobulin locus, such methods and other exemplary methods for preparing monoclonal antibodies are described herein.

In the present specification, "affinity" means the strength of the sum of non-covalent interactions between a single binding site of a molecule (for example, an antibody) and its binding partner (for example, an antigen). Unless otherwise indicated, the "binding affinity" used in this specification means the inherent binding affinity that reflects the 1:1 interaction between members of a binding pair (e.g., antibody and antigen). The affinity of a molecule X to its partner Y can usually be expressed by the equilibrium dissociation constant (Kr)). The affinity can be measured by common methods known in the art.

In this specification, human Interleukin-17A (hIL-17A) represents a human-derived protein, and its amino acid sequence is shown in SEQ ID NO: 9, wherein the underlined part represents a signal peptide.

SEQ ID NO: 9: MTPGKTSLVSLLLLLSFAIVKAGI-TIPRNPGCPNSEDKNFPRTVMVNLNIHNRN-TNTNPKRSS DYYNRSTSPWNLHRNEDPERYPSVI-WEAKCRHLGCINADGNVDYHMNSVPIQQEILVLRREP PHCPNSFRLEKILVSVGCTCVTPIVHHVA IL-17A is a pro-inflammatory cytokine produced by Th17 cells, which stimulates such as keratinocytes, fibroblasts, epithelial cells, endothelial cells, joint synovial cells, etc. by binding to its receptor IL-17RA and IL-17RC to produce IL-6, IL-8, G-CSF, GM-CSF, CXCL-1, CXCL-2, CCL-8, CCL-2, CCL-7 and other cytokines, participates in and promotes a variety of diseases mediated by abnormal immune responses, such as rheumatoid arthritis, psoriasis, multiple sclerosis, psoriatic arthritis, plaque psoriasis, ankylosing spondylitis, etc.

The monoclonal antibody of the present invention is a neutralizing antibody that specifically recognizes IL-17A. It binds to IL-17A, thereby blocking IL-17A from transducing signals and mediating biological effects through its receptor, thereby preventing and treating autoimmune diseases mediated by IL-17A.

In the present specification, "anti-human interleukin 17A monoclonal antibody" means a monoclonal antibody that can bind to human interleukin 17A with sufficient affinity so that the monoclonal antibody can be used as a diagnostic agent and/or therapeutic agent targeting human interleukin 17A.

In one embodiment, for example, as measured by radioimmunoassay (RIA), the degree of binding of the anti-human interleukin 17A monoclonal antibody to the unrelated, non-human interleukin 17A protein is less than, for example, about 10% of that of the monoclonal antibody to the human interleukin 17A protein.

In certain embodiments, the monoclonal antibody that binds to human interleukin 17A has ≤1 µM, ≤100 nM, ≤10 nM, ≤1 nM, ≤0.1 nM, ≤0.01 nM, or ≤0.001 nM (e.g., $10^{-8}$ M or lower, $10^{-8}$ M to $10^{-13}$ M, $10^{-9}$ M to $10^{-13}$ M) equilibrium dissociation constant ($K_D$).

In one embodiment, the amino acid sequence of the heavy chain of the anti-human interleukin 17A monoclonal antibody of the present invention is shown in SEQ ID NO: 10; the amino acid sequence of the light chain is shown in SEQ ID NO: 11.

SEQ ID NO: 10 EVQLQESGPGLVKP-SETLSLTCTVSGIDLSLFYMSWIRQPPGKGLEWIGTI-HEVASSYYASWA KGRVTISKDTSKNQFSLKLSS-VTAADTAVYYCARETYSSRYPYPNIWGQGTLVTVS-SASTKG PSVFPLAPSSKSTSGGTAALGCLVKDYF-PEPVTVSWNSGALTSGVHTFPAVLQSSGLYSLSSV VTVPSSSLGTQTYICNVNHKPSNTKVDKKVE-PKSCDKTHTCPPCPAPELLGGPSVFLFPPKPK DTLMISRTPEVTCVVVDVSHEDPEVKFNWYVD-GVEVHNAKTKPREEQYNSTYRVVSVLTV LHQDWLNGKEYKCKVSNKALPAPIEKTISKAKG-QPREPQVYTLPPSRDELTKNQVSLTCLV KGFYPSDIA-

VEWESNGQPENNYKTTPPVLDSDGSFFLYSK-
LTVDKSRWQQGNVFSCSVMHE ALHNHYTQKSLSL-
SPGK SEQ ID NO: 11 DIQMTQSPSSVSAS-
VGDRVTITCQASQNIGGSLAWYQQKPGKAPKLLIY-
GASSLASGVPSRFS GSGSGTDFTLTISSLQPEDFA-
TYYCQSYNTISTYGLAFGGGTKVEIKRTVAAPSVFI-
FPPSDEQ LKSGTASVVCLLNNFYPREAKVQWKVD-
NALQSGNSQESVTEQDSKDSTYSLSSTLTLSKAD
YEKHKVYACEVTHQGLSSPVTKSFNRGEC

Wherein, SEQ ID NOs: 10 and 11 are both humanized sequences.

In this specification, "isolated" nucleic acid means a nucleic acid molecule that has been separated from a component of its natural environment. An isolated nucleic acid includes a nucleic acid molecule contained in a cell that usually contains a nucleic acid molecule, but the nucleic acid molecule is present outside the chromosome or at a chromosomal location different from its natural chromosomal location.

In the present specification, "isolated nucleic acid encoding anti-human interleukin 17A monoclonal antibody" means one or more nucleic acid molecules encoding antibody heavy and light chains, including such nucleic acid molecules in a single vector or separate vectors, and such nucleic acid molecules present in one or more locations in the host cell.

In this specification, "vector" means a nucleic acid molecule capable of amplifying another nucleic acid linked to it. The term includes a vector as a self-replicating nucleic acid structure as well as a vector integrated into the genome of a host cell into which it has been introduced. Certain vectors can direct the expression of nucleic acids to which they are operably linked. Such vectors are referred to herein as "expression vectors".

In this specification, "host cell", "host cell line" and "host cell culture" are used interchangeably and refer to cells into which exogenous nucleic acid has been introduced, including the progeny of such cells. Host cells include "transformants" and "transformed cells", which include primary transformed cells and progeny derived therefrom (regardless of the number of passages). The offspring may not be exactly the same as the parent cell in terms of nucleic acid content, but may contain mutations. The mutant progeny with the same function or biological activity screened or selected for the originally transformed cells are included in this specification.

In the present specification, "pharmaceutical composition" means a preparation that is in a form that makes the biological activity of the active ingredient contained therein effective, and that the composition does not contain additional components with unacceptable toxicity to the subject to which the formulation is to be administered.

In the present specification, "pharmaceutically acceptable carrier" means ingredients other than the active ingredient in the pharmaceutical composition, which are non-toxic to the subject.

Pharmaceutically acceptable carriers include, but are not limited to, buffers, excipients, stabilizers or preservatives.

EXAMPLE

Hereinafter, the present invention will be explained in more detail through examples. It should be understood that the present invention is not limited to these examples.

Example 1 Preparation of Anti-Human Interleukin 17A Monoclonal Antibody QX002N

The human interleukin 17A was purchased from Shanghai Novoprotein Technology Co., Ltd. for immunizing New Zealand rabbits. B cell cloning technology was used to screen out monoclonal antibodies that have inhibitory activity on human interleukin 17A. First, the cell supernatant was detected by using binding ELISA to select clones that bind to hIL-17A; then, blocking ELISA was used to detect clones that could inhibit the binding of hIL-17A to its receptor. The above immunization and screening process were entrusted to a commercial company to complete.

Eight clones were selected for recombinant expression and sequencing. And the clone 37 # was humanized. The homology alignment to human IgG germline sequences was performed using NCBI IgBlast. IgGHV4-59*01 was selected as the template for heavy chain CDR grafting, and the heavy chain CDR regions of the clone 37 # (i.e., CDR-H1 (SEQ ID No: 1), CDR-H2 (SEQ ID No: 2) and CDR-H3 (SEQ ID No: 3)) were grafted into the framework regions of IgGHV4-59*01; IGKV1-12*01 was selected as the template for light chain CDR grafting, and the light chain CDR regions of the clone 37 #(i.e., CDR-L1 (SEQ ID No: 4), CDR-L2 (SEQ ID No: 5) and CDR-L3 (SEQ ID No: 6)) were grafted into the framework regions of IGKV1-12*01; back mutations at specific sites in the framework regions were performed to obtain the variable regions of the monoclonal antibody QX002N of the present invention. Finally, the amino acid sequence of the humanized heavy chain variable region is shown in SEQ ID NO: 7; the amino acid sequence of the humanized light chain variable region is shown in SEQ ID NO: 8.

Figure 1:
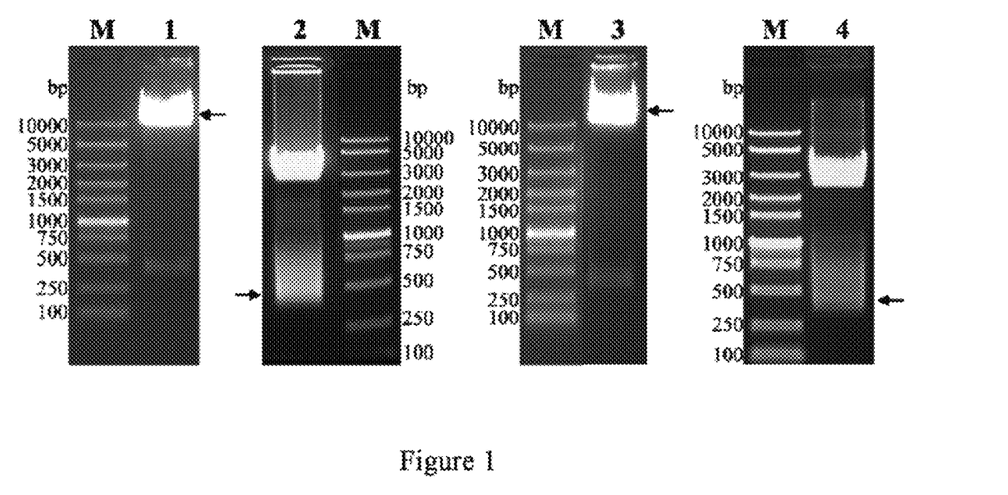
FIG. 1 is the result of nucleic acid electrophoresis, wherein, M: Marker; Lane 1: pHZDCH, HindIII/NheI; Lane 2: pUC57-37VH-Hu5, HindIII/NheI: Lane 3: pHZDCK, HindIII/BsiWI; Lane 4: pUC57-37VK-Hu2, HindIII/BsiWI.
Figure 2:
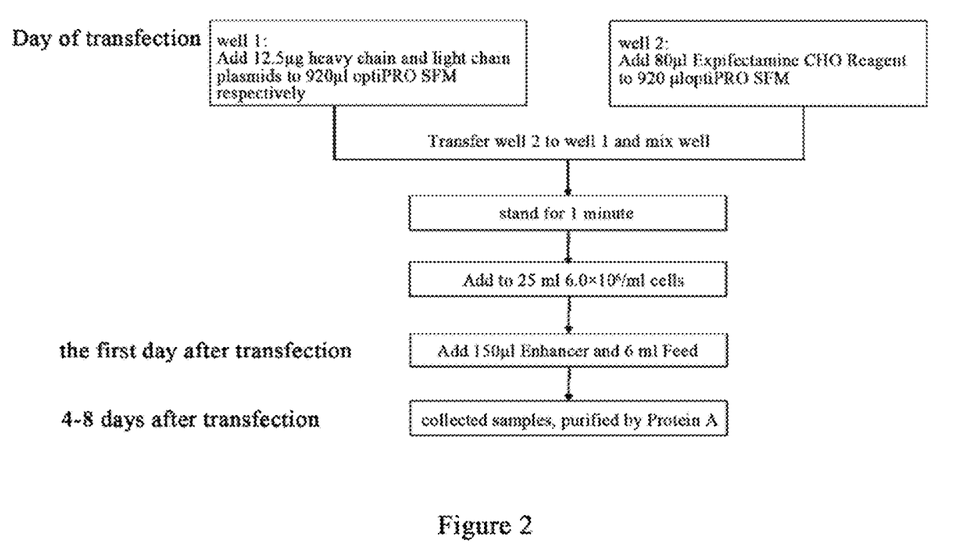
FIG. 2 is a flow chart of transient expression.

The gene sequences of the heavy chain variable region and the light chain variable region were synthesized artificially and inserted into the pUC57 vector, respectively. The gene of the heavy chain variable region and the heavy chain expression plasmid pHZDCH were digested with HindIII and NheI; the gene of the light chain variable region and the light chain expression plasmid pHZDCK were digested with HindIII and BsiWI; the T4 DNA ligase was used to insert the digested fragments into the corresponding expression plasmids, respectively; the heavy chain expression plasmid pHZDCH-37VH-Hu5 and the light chain expression plasmid pHZDCK-37VK-Hu2 were constructed. The results of double digestion of the plasmids detected by nucleic acid electrophoresis were shown in FIG. 1. According to the results in FIG. 1, it can be seen the results of double enzyme digestion of the heavy and light chain variable regions and the heavy and light chain expression plasmids of the antibody, wherein, the plasmid size of the heavy and light chains is about 10,000 bp, the variable region of the light chain is about 420 bp, and the variable region of the heavy chain is about 441 bp. The heavy chain and light chain expression plasmids with the correct sequence were co-transfected into ExpiCHO—S cells. The day before transfection, the ExpiCHO—S cells were diluted to $3\times10^6$ cells/ml for passage before transfection. On the day of transfection, dilute the cell density to $6\times10^6$ cells/mi, and pack 25 ml of cells in a 125 ml shake flask, and wait for transfection. The transfection and expression process are shown in FIG. 2.

Figure 3:
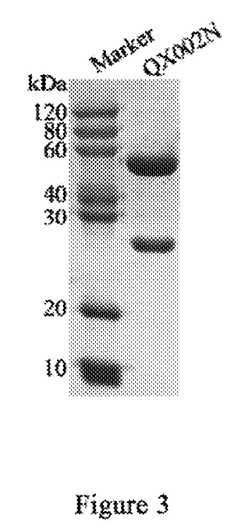
FIG. 3 is a diagram of protein electrophoresis detection.

On the 7th day after transfection, the culture supernatant was harvested and purified with Protein A in one step. The purified antibody was detected by SDS-PAGE electrophoresis and named as QX002N. The result of the antibody detected by protein electrophoresis is shown in FIG. 3. The protein electrophoresis was performed on a denatured reducing gel. The result in FIG. 3 shows that there are two bands. The sizes of the two bands are about 50 kDa and 25 kDa respectively, which are consistent with the theoretical molecular weights of the heavy chain (49.3 kDa) and light chain (23.2 kDa).

Example 2 Determination of Equilibrium Dissociation Constant ($K_D$)

Biacore T200 was used to detect the affinity of QX002N binding to hIL-17A, and all processes were performed at 25° C. The Protein A was chemically coupled to the CM5 chip, and an appropriate amount of antibody was immobilized by the capture method, so that the Rmax was less than 50 RU, and the capture flow rate was 10 μl/min. The antigen was gradually diluted, and the flow rate of the instrument was switched to 30 μl/min. The diluted antigen was flowed through the reference channel and the channel of immobilized antibody in sequence from low to high concentration, and the running buffer was flowed through as a negative control. After each binding and dissociation was completed, the chip was regenerated with glycine, pH1.5. Fitting was performed with the build-in software in the instrument according to a 1:1 binding model. The association rate constant $k_a$, the dissociation rate constant $k_d$, and the equilibrium dissociation constant $K_D$ values of the antibody were calculated.

In addition, the affinity of QX002N was compared with the currently commercialized antibodies against hIL-17A, i.e., Ixekizumab (IXE) and Secukinumab (SEC). The detection method for known antibodies is the same as the detection method for QX002N. The results are shown in the table below.

Wherein, Ixekizumab (IXE) and Secukinumab (SEC) were obtained by purchasing commercially available drugs, respectively.

| Sample name | $k_a$ ($10^6$ $M^{-1}S^{-1}$) | $k_d$ ($10^{-5}S^{-1}$) | $K_D$ (pM) |
|---|---|---|---|
| QX002N | 3.35 | 2.36 | 7.07 |
| Ixekizumab (IXE) | 1.70 | 2.58 | 15.35 |
| Secukinumab (SEC) | 0.24 | 6.55 | 339.00 |

Each sample was tested twice and the average value was calculated.

Example 3 the Anti-Human Interleukin 17A Monoclonal Antibody Prepared in Example 1 Inhibits the Activity of Cells Induced by Human Interleukin 17A or its Mutants 3.1 Determine the Dilution Factor of hIL-17A Mutant Transient Expression Supernatant Since the yield of hIL-17A mutant in mammalian cell expression system was too low to be purified, the supernatant described in FIG. 2 was used directly for cell-based inhibition assay. However, the proper dilution factor of the supernatants should be determined by cell-based assay.

hIL-17A can induce HEK-Blue™ IL-17 Cells to release secreted embryonic alkaline phosphatase (SEAP). Detect the released amount of SEAP induced by the hIL-17A standard at different concentrations and draw the concentration curve. The released amount of SEAP close to upper platform period was induced by 3 ng/ml of hIL-17A. Therefore 3 ng/ml was selected as the working concentration.

Supernatants of different hIL-17A mutants were gradually diluted, and the released amount of SEAP induced by hIL-17A mutants of different dilutions was detected. The dilution factor was selected for cell-based inhibition assay, while the released amount of SEAP induced by diluted hIL-17A mutants was the same as that induced by 3 ng/ml of hIL-17A standard.

Figure 4:
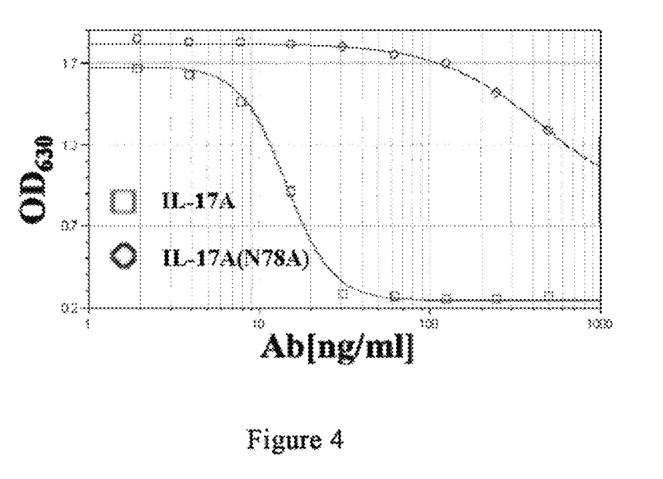
FIG. 4 is a graph showing the results of QX002N inhibiting hIL-17A and hIL-17A mutant (N78A)-induced SEAP release.

3.2 Epitope Study of the Antibodies Binding to hIL-17A by Cell-Based Neutralizing Assay The antibodies with different concentration gradients were incubated with the pre-diluted hIL-17A mutant (N78A) supernatant and 3 ng/mi of hIL-17A standard for 2 hours, respectively. 2 hours later, the above incubations were transferred to a 96-well cell culture plate pre-seeded with HEK-Blue™ IL-17 Cells. The expression of SEAP in the cells was detected 24 hours later, and data were analyzed and plotted using four parameter logistic curve fitting via SoftMax Pro (see FIG. 4). The antibody can inhibit the release of SEAP induced by hIL-17A standard. If the antibody cannot or cannot completely inhibit the release of SEAP induced by the hIL-17A mutant, it indicates that the antibody cannot bind to the hIL-17A mutant, and the corresponding site of the mutation is the epitope of the antibody; if the antibody can inhibit the release of SEAP induced by the hIL-17A mutant, it indicates that the antibody can bind to the hIL-17A mutant, and the site corresponding to the mutation is not the epitope of the antibody.

Figure 5:
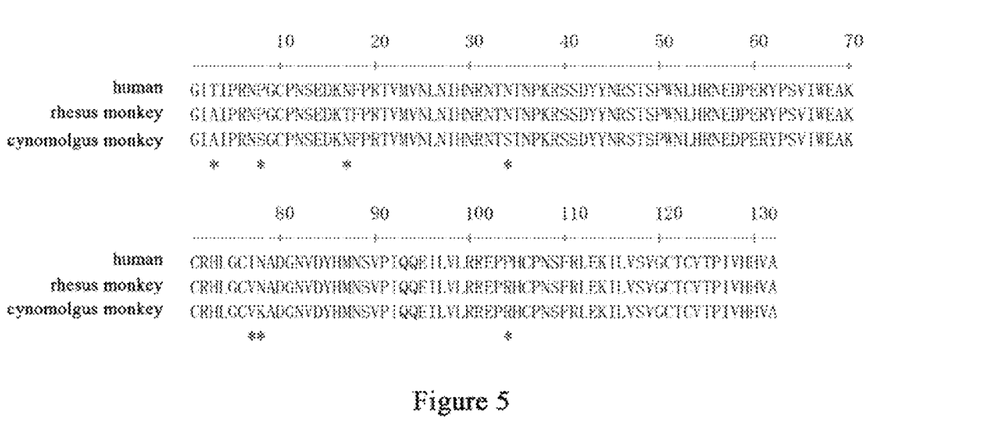
FIG. 5 is a diagram showing the results of the amino acid sequence alignment of IL-17A in humans, rhesus monkeys and cynomolgus monkeys.
Figure 6:
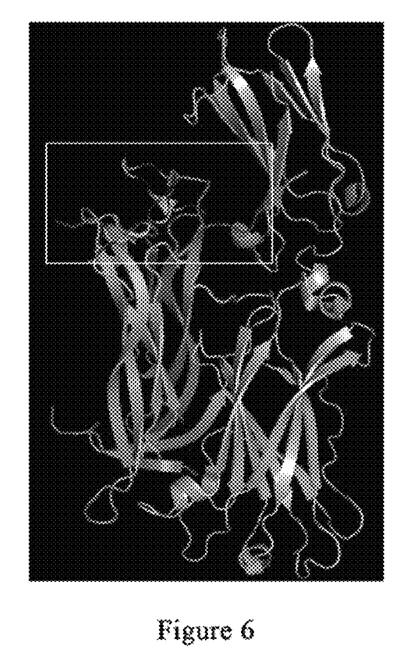
FIG. 6 is a diagram showing the position of the epitope recognized by QX002N and IXE in the crystal structure of the complex of IL-17A and its receptor. The epitope on IL-17A recognized by QX002N and IXE is represented by a box. The homodimer on the left is the structure of IL-17A, and the right is the structure of the IL-17A receptor.
Figure 7:
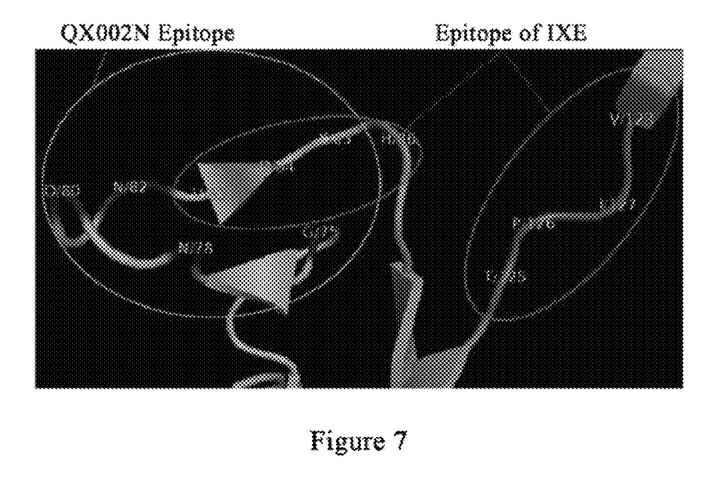
FIG. 7 is a partial enlarged view in the box of FIG. 6.
Figure 8:
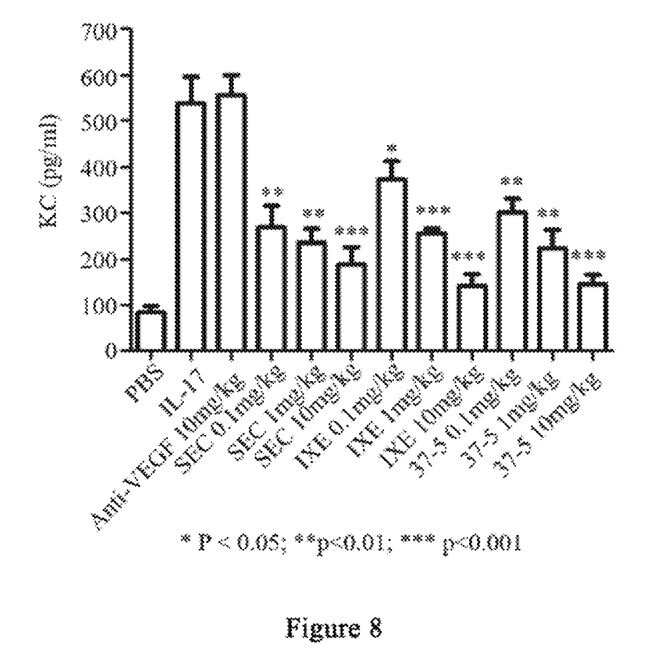
FIG. 8 is a graph showing the experimental results of QX002N inhibiting IL-17A-induced KC release in mice.

The result shows that QX002N could not completely inhibit the SEAP release induced by N78A mutated hIL-17A. Meanwhile, QX002N could not block the release of SEAP induced by cynomolgus IL-17A instead of rhesus IL-17A. Therefore. N78 of hIL-17A is the epitope of QX002N. It should be noted that Figure S shows the alignment result of the IL-17A amino acid sequences of human, rhesus and cynomolgus. The 78th position of human and rhesus IL-17A is Asparagine (N), but the 78th position of cynomolgus IL-17A is Lysine (K).

For SEC and IXE, the same method was used for detection. The results show that both SEC and IXE can bind to hIL-17A mutant (N78A) and cynomolgus IL-17A. Therefore, QX002N has different epitopes from SEC and IXE.

Example 4 Determine the hIL-17A Epitope Recognized by the Anti-Human Interleukin 17A Monoclonal Antibody Prepared in Example 1

Experimental results show that D80GNVDYH86 of hIL-17A may be an epitope of QX002N. In order to determine the epitope region targeted by QX002N, single point mutations were performed in D80GNVDYH86 of hIL-17A and its adjacent sites. If the antibody cannot or cannot completely inhibit the release of SEAP induced by the hIL-17A mutant, it means that the antibody cannot bind to the hIL-17A mutant, and the corresponding site of the mutation is the epitope targeted by the antibody.

The results are shown in Table 1. It can be determined that the epitope region targeted by QX002N is G75XXN78XD80XN82V83D84Y85, wherein X represents any amino acid, and the number behind the one-letter symbol of the amino acid represents the position of the amino acid in hIL-17A.

TABLE 1

| The epitope on IL-17A bound by QX002N | | |
|---|---|---|
| Site | Amino acid | Mutation | Cell-based neutralizing activity |
| 72 | R | A | Inhibition |
| 73 | H | A | Inhibition |
| 74 | L | A | Inhibition |
| 75 | G | R/S/N | Incomplete inhibition |
| 76 | C | S/G | No expression |
| 77 | I | A | Inhibition |

TABLE 1-continued

The epitope on IL-17A bound by QX002N

| Site | Amino acid | Mutation | Cell-based neutralizing activity |
|---|---|---|---|
| 78 | N | A | Incomplete inhibition |
| 79 | A | G/R/B/N/S/L | Inhibition |
| 80 | D | A | No inhibition |
| 81 | G | A/R/S/L | Inhibition |
| 82 | N | A | No inhibition |
| 83 | V | G | No inhibition |
| 84 | D | A | No inhibition |
| 85 | Y | A | No inhibition |
| 86 | H | A | Inhibition |
| 87 | M | A | Inhibition |
| 88 | N | A | Inhib

The invention claimed is:

1. An isolated anti-human interleukin 17A monoclonal antibody, which comprises three heavy chain complementarity determining regions (CDR-H1, CDR-H2 and CDR-H3) and three light chain complementarity determining regions (CDR-L1, CDR-L2 and CDR-L3), wherein,
   (a) an amino acid sequence of CDR-H1 is the amino acid sequence shown in SEQ ID NO: 1;
   (b) an amino acid sequence of CDR-H2 is the amino acid sequence shown in SEQ ID NO: 2;
   (c) an amino acid sequence of CDR-H3 is the amino acid sequence shown in SEQ ID NO: 3;
   (d) an amino acid sequence of CDR-L1 is the amino acid sequence shown in SEQ ID NO: 4;
   (e) an amino acid sequence of CDR-L2 is the amino acid sequence shown in SEQ ID NO: 5; and
   (f) an amino acid sequence of CDR-L3 is the amino acid sequence shown in SEQ ID NO: 6.

2. An isolated nucleic acid, encoding the monoclonal antibody according to claim 1.

3. A pharmaceutical composition, comprising the monoclonal antibody according to claim 1 and a pharmaceutically acceptable carrier.

4. A method of treating an autoimmune disease, which includes:
   the monoclonal antibody according to claim 1 is administered to a subject in need thereof.

5. The method according to claim 4, wherein the autoimmune disease is rheumatoid arthritis, psoriasis, Crohn's disease, multiple sclerosis, psoriatic arthritis, plaque psoriasis and/or ankylosing spondylitis.

6. The isolated anti-human interleukin 17A monoclonal antibody according to claim 1, comprising a heavy chain variable region with an amino acid sequence shown in SEQ ID NO:7 and a light chain variable region with an amino acid sequence shown in SEQ ID NO:8.

7. The monoclonal antibody according to claim 6, comprising a heavy chain with an amino acid sequence shown in SEQ ID NO: 10 and a light chain with an amino acid sequence shown in SEQ ID NO:11.

8. An isolated nucleic acid, encoding the monoclonal antibody according to claim 6.

9. A pharmaceutical composition, comprising the monoclonal antibody according to claim 6 and a pharmaceutically acceptable carrier.

10. A method of treating an autoimmune disease, which includes:
    the monoclonal antibody according to claim 6 is administered to a subject in need thereof.

11. The method according to claim 10, wherein the autoimmune disease is rheumatoid arthritis, psoriasis, Crohn's disease, multiple sclerosis, psoriatic arthritis, plaque psoriasis and/or ankylosing spondylitis.

12. The isolated anti-human interleukin 17A monoclonal antibody according to claim 1, which binds to an epitope comprising amino acid residues 98-108 in the amino acid sequence of SEQ ID NO: 9.

* * * * *

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: artificially synthesized sequence

<400> SEQUENCE: 1

Leu Phe Tyr Met Ser
1               5

<210> SEQ ID NO 2
<211> LENGTH: 15
<212> TYPE: PRT
<213> ORGANISM: Artificial Sequence
<220> FEATURE:
<223> OTHER INFORMATION: artificially synthesized sequence

<400> SEQUENCE: 2

Thr Ile His Glu Val Ala Ser Ser Tyr Tyr Ala Ser Trp Ala Lys
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: artificially synthesized sequence

<400> SEQUENCE: 3

Glu Thr Tyr Ser Ser Arg Tyr Pro Tyr Pro Asn Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: artificially synthesized sequence

<400> SEQUENCE: 4

Gln Ala Ser Gln Asn Ile Gly Gly Ser Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: artificially synthesized sequence

<400> SEQUENCE: 5

Gly Ala Ser Ser Leu Ala Ser
1               5

<210> SEQ ID NO 6
<211> LENGTH: 12
<212> TYPE: PRT
<213> ORGANISM: Artificial Sequence
<220> FEATURE:
<223> OTHER INFORMATION: artificially synthesized sequence

<400> SEQUENCE: 6

Gln Ser Tyr Asn Thr Ile Ser Thr Tyr Gly Leu Ala
1               5                   10

<210> SEQ ID NO 7
<211> LENGTH: 120
<212> TYPE: PRT
<213> ORGANISM: Artificial Sequence
<220> FEATURE:
<223> OTHER INFORMATION: artificially synthesized sequence

<400> SEQUENCE: 7

Glu Val Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Leu Phe
            20                  25                  30

Tyr Met Ser Trp Ile Arg Gln Pro Pro Gly Lys Gly Leu Glu Trp Ile
        35                  40                  45

Gly Thr Ile His Glu Val Ala Ser Ser Tyr Tyr Ala Ser Trp Ala Lys
    50                  55                  60

Gly Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Tyr Ser Ser Arg Tyr Pro Tyr Pro Asn Ile Trp Gly Gln
            100                 105                 110

Gly Thr Leu Val Thr Val Ser Ser
        115                 120

<210> SEQ ID NO 8
<211> LENGTH: 110
<212> TYPE: PRT
<213> ORGANISM: Artificial Sequence
<220> FEATURE:
<223> OTHER INFORMATION: artificially synthesized sequence

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Gly Gly Ser
            20                  25                  30

Leu Ala Trp Tyr Gln Gln Lys Pro Gly Lys Ala Pro Lys Leu Leu Ile
        35                  40                  45

Tyr Gly Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asn Thr Ile Ser Thr
                85                  90                  95

Tyr Gly Leu Ala Phe Gly Gly Gly Thr Lys Val Glu Ile Lys
            100                 105                 110

<210> SEQ ID NO 9
<211> LENGTH: 155
<212> TYPE: PRT
<213> ORGANISM: Homo sapiens

<400> SEQUENCE: 9

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

```
Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
            130                 135                 140

Thr Cys Val Thr Pro Ile Val His His Val Ala
145                 150                 155

<210> SEQ ID NO 10
<211> LENGTH: 450
<212> TYPE: PRT
<213> ORGANISM: Artificial Sequence
<220> FEATURE:
<223> OTHER INFORMATION: artificially synthesized sequence

<400> SEQUENCE: 10

Glu Val Gln Leu Gln Glu Ser Gly Pro Gly Leu Val Lys Pro Ser Glu
 1               5                  10                  15

Thr Leu Ser Leu Thr Cys Thr Val Ser Gly Ile Asp Leu Ser Leu Phe
            20                  25                  30

Tyr Met Ser Trp Ile Arg Gln Pro Pro Gly Lys Gly Leu Glu Trp Ile
            35                  40                  45

Gly Thr Ile His Glu Val Ala Ser Ser Tyr Tyr Ala Ser Trp Ala Lys
 50                  55                  60

Gly Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
            85                  90                  95

Arg Glu Thr Tyr Ser Ser Arg Tyr Pro Tyr Pro Asn Ile Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 11
<211> LENGTH: 217
<212> TYPE: PRT
<213> ORGANISM: Artificial Sequence
<220> FEATURE:
<223> OTHER INFORMATION: artificially synthesized sequence

<400> SEQUENCE: 11

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Gly Gly Ser
            20                  25                  30

Leu Ala Trp Tyr Gln Gln Lys Pro Gly Lys Ala Pro Lys Leu Leu Ile
        35                  40                  45

Tyr Gly Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asn Thr Ile Ser Thr
                85                  90                  95

Tyr Gly Leu Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140
```

```
Arg Glu Ala Lys Val Gln Trp Lys Val Asp Asn Ala Leu Gln Ser Gly
145             150                 155                 160

Asn Ser Gln Glu Ser Val Thr Glu Gln Asp Ser Lys Asp Ser Thr Tyr
                165             170                 175

Ser Leu Ser Ser Thr Leu Thr Leu Ser Lys Ala Asp Tyr Glu Lys His
            180             185                 190

Lys Val Tyr Ala Cys Glu Val Thr His Gln Gly Leu Ser Ser Pro Val
        195             200                 205

Thr Lys Ser Phe Asn Arg Gly Glu Cys
    210             215
```